United States Patent [19]

Kao

[11] 3,939,228

[45] Feb. 17, 1976

[54] PROCESS FOR PRODUCING PHOSPHAZENE COMPOUND

[75] Inventor: James T. F. Kao, Baton Rouge, La.

[73] Assignee: Ethyl Corporation, Richmond, Va.

[22] Filed: Apr. 4, 1973

[21] Appl. No.: 347,833

[52] U.S. Cl. ............................ 260/973; 260/927 N
[51] Int. Cl.$^2$ .......................................... C07F 9/15
[58] Field of Search ...................... 260/973, 927 N

[56] References Cited
UNITED STATES PATENTS

| | | | |
|---|---|---|---|
| 2,971,974 | 2/1961 | Blair | 260/973 X |
| 3,005,001 | 10/1961 | Senkbeil | 260/973 X |
| 3,206,494 | 9/1965 | Lund et al. | 260/973 X |
| 3,394,205 | 7/1968 | Bilger | 260/973 |
| 3,795,526 | 4/1974 | Bergeron | 260/927 N X |

*Primary Examiner*—Anton H. Sutto
*Attorney, Agent, or Firm*—Donald L. Johnson; John F. Sieberth; James M. Pelton

[57] ABSTRACT

A process for manufacture of phosphazene compounds in a liquid aliphatic hydrocarbon reaction medium providing process advantages by reacting therein an alkali metal alkoxide, phenoxide or thiol derivative with a phosphonitrilic halide.

8 Claims, No Drawings

PROCESS FOR PRODUCING PHOSPHAZENE COMPOUND

BACKGROUND OF THE INVENTION

This invention relates to processes for producing phosphazene compounds, particularly alkoxy and aryloxy substituted phosphazene compounds. Also the mercapto analog of these alkoxy and aryloxy phosphazene compounds are included. Recent interest has developed in such phosphazene compounds for use in high temperature materials, polymers and flame retardants.

In general, processes for producing alkoxy, aryloxy and mercapto-substituted phosphazene compounds are known. For example, the reaction of a halophosphazene or phosphonitrilic halide with alcohols or thiols is known and described at considerable length in Allcock, *Phosphorus-Nitrogen Compounds*, Academic Press, New York, 1972. According to Allcock, the reaction medium has a great influence on the reaction, affecting such variables as time of reaction, type of product produced, and purity of the product. Various solvents are known as reaction media for the substitution reactions for alcohols and thiols on phosphazene compounds. Typical of these are diethyl ether, tetrahydrofuran, dioxane, benzene, toluene, xylene, dimethylformamide, fluorocarbon-t-butylamine, pyridine and excess amounts of the alcohol or thiol used as a reagent. Unfortunately, many of these solvents provide problems in commercial processes because of emulsion formation on subsequent water-washing of the substituted phosphazene product. This causes problems in overall yield through loss of product and problems of solvent recovery which are unacceptable in commercial processes.

Also in such substitution reactions, the solvent used in the production of the phosphonitrilic halide itself may be present, which is different from the desired solvent useful in the substitution reaction. Thus, a mixed solvent system may result in the substitution reaction. This additional solvent must be removed and a further solvent removal step is required. Mixed solvent systems present difficult problems of solvent separation from product and solvent recovery. Solvents used in the production of phosphonitrilic chloride are symmetrical tetrachloroethane, monochlorobenzene, dichlorobenzene, nitrobenzene and the like. Thus, these solvents must be completely separated from the phosphonitrilic halide produced, resulting in extra process costs and capital investment, or they are used with the phosphonitrilic halide in the substitution reaction, causing difficult separation problems which also increase process costs and capital investment.

The process of the present invention uses a reaction medium which does not adversely affect yield. It does not require separation of the solvent used in preparing the starting phosphonitrilic halide. Further, the reaction medium can be easily separated from the product and other solvents. These features of the invention provide definite processing advantages for the production of phosphazene compounds.

SUMMARY OF THE INVENTION

According to this invention phosphazene compounds are prepared by a process of reacting an alkali metal alkoxide or phenoxide with a phosphonitrilic halide in a reaction medium comprising a liquid aliphatic hydrocarbon. A preferred reaction medium comprises a paraffinic hydrocarbon. A more preferred reaction medium consists essentially of a liquid mixture of a liquid aliphatic hydrocarbon and an inert halohydrocarbon solvent.

In a preferred embodiment of the process of this invention, phosphazene compounds are manufactured by a process of reacting an alkali metal and an alcohol or phenol reactant in a liquid saturated aliphatic hydrocarbon, producing a slurry of the alkoxide or phenoxide in the hydrocarbon and then reacting a phosphonitrilic halide with the alkoxide or phenoxide in a reaction medium comprising the liquid aliphatic hydrocarbon.

In another preferred embodiment of the process of this invention, phosphazene compounds are manufactured by reacting an alkali metal or phenoxide provided in a liquid aliphatic hydrocarbon reaction medium with a phosphonitrilic halide provided in an aromatic halohydrocarbon reaction medium.

In a still further preferred embodiment of the process of this invention, phosphazene compounds are manufactured by a process of a. forming a slurry of an alkali metal alkoxide or phenoxide by reacting an alkali metal with an alcohol or phenol reactant in a liquid paraffinic hydrocarbon reaction medium;

b. forming a solution of a phosphonitrilic halide by reacting ammonia or ammonium halide with a phosphorus halide in an inert liquid diluent which is different from the liquid paraffinic hydrocarbon in step (a) above;

c. inter-mixing the slurry of (a) and the solution of (b) whereby a phosphazene product and an alkali metal halide by-product are formed in a reaction mixture which comprises the liquid paraffinic hydrocarbon and the inert liquid diluent;

d. separating the alkali metal halide by-product from the reaction mixture;

e. separating the reaction mixture from the phosphazene product; and f. separating the reaction mixture into the liquid paraffinic hydrocarbon for recycle to (a) and the inert liquid diluent for recycle to (b).

DESCRIPTION OF THE PREFERRED EMBODIMENTS

In accordance with the process of this invention there is reacted a phosphonitrilic halide with an alkali metal alkoxide or phenoxide or thiol derivative thereof in an aliphatic hydrocarbon reaction medium. The phosphonitrile halide used as a starting material according to this process can be any suitable halide, for example, fluoride, chloride, bromide or mixed halide, with the chloride being preferred. Such phosphonitrilic halide can be prepared according to processes known in the art. For example, Allcock, *Phosphorus-Nitrogen Compounds*, Academic Press, New York (1972), in Chapter 4, Pages 97–133, gives a general survey of the methods for preparation of phosphazenes, particularly halophosphazenes or phosphonitrilic halides. Particularly described is the reaction between halophosphoranes and ammonium halides. This particular portion of Allcock is incorporated by reference as if fully set forth herein.

In addition, U.S. Pat. No. 3,367,750 to Jaszka et al., which is hereby incorporated by reference as if fully set forth, provides a process for producing phosphonitrilic chlorides by reacting phosphorus pentachloride in a solvent with ammonia and hydrogen chloride gas. U.S. Pat. No. 3,656,916 to Schiedermaier et al. produces phosphonitrilic chlorides by reacting phosphorus pentachloride with ammonia in an inert solvent using a particular rate of ammonia feed. The Schiedermaier et al. process is also suitable for producing phosphonitrilic chlorides useful in this invention and is incorporated herein by reference as if fully set forth. U.S. Pat. No. 3,658,487 to Wunsch et al. teaches a process for producing phosphonitrilic chlorides by reacting chlorine and ammonia simultaneously with elementary phosphorus in an inert solvent and is incorporated by reference as if fully set forth. Thus, it can be seen that a wide variety of processes can be used to produce phosphonitrilic chlorides which are suitable for the process of this invention as a starting material.

In accordance with this invention the phosphonitrilic chloride starting material can be any desired cyclic, linear, cyclic-linear mixture or combination of cyclic and linear which may be desired as a backbone polymer in the final product. Preferably the starting phosphonitrilic halide is a high cyclic material; however, materials having a large proportion of linears or substantially equivalent amounts of linears and cyclics can be obtained. As is recognized by the art, the cyclics may be trimer, tetramer, pentamer or higher cyclic oligomers of phosphonitrilic halides. The linear phosphonitrilic halide polymers can have any chain length desired; although in some instances, some materials are insoluble in the subsequent reaction media.

Generally, the final phosphazene products produced will be similar to the starting phosphonitrilic halide since the nature of the substitution reaction will not alter the polymer backbone.

The phosphonitrilic halide is reacted with an alkali metal alkoxide or phenoxide or a thiol derivative thereof. According to this invention, the starting alkali metal alkoxide, phenoxide or thiol derivative thereof may be produced in the conventional manner. Such processes are known and described in, for example, Kirk-Othmer, *Encyclopedia of Chemical Technology*, Second Edition, Volume 1, Pages 832–850. Illustrative is a process for producing sodium methoxide described at pages 845–848 of Kirk-Othmer, supra, which is hereby incorporated by reference as if fully set forth. As described therein the alkali metal is added to a reaction vessel and heated until it melts. To the molten alkali metal is added the particular alcohol, phenol or thiol derivative desired to be substituted on the final phosphazene product. Such reaction can be carried out in the presence or absence of a solvent. As described hereinafter the presence of a solvent is particularly desired in order to obtain certain process advantages in accordance with this invention. The alcohol, phenol or thiol derivative thereof may be any particular compound which will react with the alkali metal to form an alkoxide which can subsequently be reacted with the phosphonitrilic halide. Typical examples of alcohols useful according to this invention are methanol, ethanol, propanol, butanol, pentanol, hexanol and the like. Typical of the phenols are phenol and alkyl-substituted derivatives thereof. Thiol derivatives of these materials are also contemplated according to the process of this invention. Moreover, any substituents such as a lower alkyl group having up to about 6 carbon atoms, halogens or the like which do not interfere with the subsequent substitution reaction on phosphazene may be used.

Preferably lower alcohols, for example, alcohols having from one to about six carbon atoms are preferred. More preferred alcohols are lower aliphatic alcohols having from one to about six carbon atoms. Still more preferred alcohols are lower saturated aliphatic alcohols, particularly those having from one to four carbon atoms. Theoretically, unsaturated aliphatic alcohols would also be useful. However, the reactive double bond does not permit practical utilization of such materials.

The alkali metal can be any suitable alkali metal which reacts completely with the alcohol used. Typical are lithium, sodium and potassium, with sodium being preferred. The reaction produces an alkali metal alkoxide, phenoxide or thiol derivative. Of course, the preferred starting material is a sodium alkoxide, phenoxide or thiol derivative. More preferred is a starting sodium alkoxide having from one to about six carbon atoms. Most highly preferred is sodium propoxide.

The reaction of phosphonitrilic halide, preferably the chloride, and sodium alkoxide, phenoxide or thiol derivative, preferably sodium propoxide, is carried out in a suitable reaction medium. It has been found that a reaction medium which gives process advantages is one comprising an aliphatic hydrocarbon. The aliphatic hydrocarbon is one which is normally liquid, although some of the normally gaseous hydrocarbons can be used under pressure. However, the pressure should not be such as to retard the reaction. Preferably the reaction medium comprises a liquid aliphatic hydrocarbon. More preferably, the reaction medium is a paraffinic hydrocarbon. Particularly, paraffinic hydrocarbons having from about six to about nine carbon atoms. More preferred are paraffinic hydrocarbons boiling in the range of from about 70° to 150°C, and more particularly preferred are paraffinic hydrocarbons boiling within the range of from about 90° to about 130°C. Typical of such hydrocarbons are n-hexane and one of its isomers, 2-methylpentane; n-heptane and its various isomers, for example, methylhexane, ethylpentane, dimethylpentane and the like; n-octane and its various isomers such as methylheptane, dimethylhexane, ethylhexane, ethylmethylpentane and the like; n-nonane and its various isomers, such as methyloctane, dimethylheptane, ethylheptane, trimethylhexane, methylethylhexane, propylhexane and the like. Moreover, cyclic compounds may also be used. For example, cyclohexane, dimethylcyclohexane, methylcyclohexane, cycloheptane and the like are suitable hydrocarbon materials for use as the reaction medium in the process of this invention. Unsaturated hydrocarbons may also be used; however they are not preferred since the olefinic bond is somewhat reactive under the conditions of the reaction. Of the paraffinic hydrocarbons the most preferred for use as a reaction medium is n-heptane or n-octane or a mixture of n-heptane and n-octane. Also various paraffinic hydrocarbon fractions may be used as the reaction medium in the process of this invention, for example, kerosene, ligroin and the like.

In a particularly advantageous embodiment according to this invention, the reaction medium is not a single component or range of components boiling within a particular temperature range, but contains at least two distinct solvents which in combination provide an advantageous reaction medium for this process. Accordingly, a preferred embodiment of this invention is one in which the reaction of a phosphonitrilic halide and sodium alkoxide, phenoxide or thiol derivative is carried out in a reaction consisting essentially of a liquid mixture of a liquid aliphatic hydrocarbon and an inert halohydrocarbon solvent. The halohydrocarbons are known as solvents for the reaction of phosphoranes and ammonium chloride or ammonia to produce the starting phosphonitrilic halides. However, these materials were thought unsuitable for the subsequent substitution reaction to produce the alkoxy, phenoxy or thiol derivatives of the phosphonitrilic halide. However, it has now been found that the combination of a liquid aliphatic hydrocarbon and a halohydrocarbon solvent provides a highly desirable reaction medium.

Generally, halohydrocarbon solvents such as haloaliphatic and aromatic hydrocarbon compounds are useful solvents for production of phosphonitrilic halides. Such compounds as symmetrical tetrachloroethane, monochlorobenzene, dichlorobenzene and the like are typical. Although symmetrical tetrachloroethane provides good reaction at short reaction times in laboratory processes, its toxicity and cost is prohibitive in commercial processes. Therefore, the haloaromatic hydrocarbon compounds are preferred as the additional solvent in the reaction medium of this invention. Particularly preferred are the chlorinated aromatic hydrocarbons. Most preferred are monochlorobenzene and dichlorobenzene with monochlorobenzene being most highly preferred. Thus, a highly preferred embodiment of the reaction medium according to this invention is one in which the hydrocarbon compound is a paraffinic hydrocarbon having from about six to about nine carbon atoms and the halohydrocarbon solvent is chlorobenzene. In another preferred embodiment of this invention the reaction medium consists essentially of a paraffinic hydrocarbon having a boiling point in the range of from about 70° to about 150°C and a halohydrocarbon solvent which is chlorobenzene. A still further preferred embodiment of this invention is a process in which the reaction medium consists essentially of a liquid aliphatic hydrocarbon which is heptane or octane or a mixture thereof and a halohydrocarbon which is chlorobenzene.

The reaction of the phosphonitrilic halide and the sodium alkoxide, phenoxide or thiol derivative is carried out under conditions suitable for substituting halide by the alkoxide, phenoxide or thiol derivative onto the phosphorus atom of the phosphorus-nitrogen structure. Either fully or partially substituted compounds may be produced depending on conditions and the relative reactivities of the reactants. Preferably the phosphorus atom is substantially fully substituted in the phosphorus-nitrogen structure. Although in some cases a partially substituted product is desirable, for example, phosphazene polymers which are subsequently crosslinked. Therefore, variations of the reaction temperature, time and concentration of the reactants will affect the degree of substitution. Generally, longer reaction times and higher temperatures lead to more completely substituted phosphazene compounds. Usually, it is sufficient to react stoichiometric amounts of reactants, but an excess of the alkoxide, phenoxide or thiol derivative can be used to insure substantially complete substitution of the halide atom. On the other hand, if only partially substituted phosphazenes are desired, a less than stoichiometric amount of the alkoxide, phenoxide or thiol derivative is used. By stoichiometric amount is meant that two alkoxide, phenoxide or thiol radicals will substitute for the halide atoms on each phosphorus atom in the phosphorus-nitrogen structure resulting in a fully substituted phosphazene product.

The mode of addition also can affect the degree of substitution of the phosphorus-nitrogen structure. For substantially complete substitution, the phosphonitrilic halide should be added to the alkali metal alkoxide, phenoxide or thiol derivative. The large initial excess or the alkoxide, phenoxide or thiol derivative facilitates substantially complete substitution of phosphorus atoms. Likewise the reverse addition, i.e., the addition of the alkali metal alkoxide, phenoxide or thiol derivative to the phosphonitrilic halide provides a large initial excess of the phosphonitrilic chloride and leads to less than complete substitution, especially when an insufficient amount of the alkali metal alkoxide, phenoxide or thiol derivative is employed. Not only the mode of addition but the rate of addition may affect the amount of substitution. Again, this appears to be a function of the initial excess of one reactant over the other. Thus, when a fast rate of addition is employed the products are not completely substituted. However, the use of a slow addition of one reactant to the other leads to substantially complete substitution.

It has been found that the addition of the reactants can take place in a manner which allows substantially complete substitution. Generally, the time of addition is less than that required for complete reaction. Preferably, the addition rate can be from about 1 to about 10 moles of phosphonitrilic chloride per mole of alkali metal alkoxide, phenoxide or thiol derivatives per hour. Usually the addition will be completed within about one hour or less depending on the size of reaction vessel and the amount of reactant employed.

The reaction temperature used is generally that sufficient to give a good rate of reaction. Usually moderate temperatures are employed although temperatures as low as ambient temperature do not facilitate the reaction and temperatures which are higher than room temperature are preferred. Of course, the temperature used will to some degree depend upon the reactants employed, the ability of the reaction equipment to transfer heat and the degree of agitation employed. Preferably the temperature should be high enough to facilitate reaction without causing excessive heating costs or requiring expensive capital equipment. However, the temperature should not be so low as to require unduly long reaction times resulting in lower capacity. Moreover, the temperature of the reaction should not be so high as to cause degradation of any of the reactants, the reaction medium or products produced. In general, the temperature can be in the range of about 70° to about 150°C or higher, if pressure reaction equipment is employed. Preferably, temperatures about 70° to about 130°C are used. Most preferably the reaction temperature can range from about 90° to about 120°C. Of course, temperatures both higher and lower may be employed but are not highly practical for reasons of operating cost, lower yield, increased capital investment, or production of undesired by-products.

The reaction of the phosphonitrilic halides and the alkali metal alkoxide, phenoxide or thiol derivative is carried out for a time sufficient to allow the desired degree of substitution. The time of reaction is not a truly independent variable but depends on the degree of substitution desired, the temperature of the reaction and the reactants involved. According to this invention, reaction times from about one to about six hours can be used. Preferably, the reaction is allowed to proceed for from about two to about four hours and, more preferably, reaction times of from about three to about four hours are typical. Such reaction times do not include the time required for addition of the reactants or bringing the reaction mass up to the desired reaction temperature.

For more efficient reaction, better contact of the reactants and adequate heat transfer the reaction mass is preferably agitated. Generally, this may be accomplished by conventional means, for example, a stirrer, mixer or other device may be used to attain sufficient degree of agitation. The type or degree of agitation is not critical but well within the scope of the art and practical engineering knowledge.

Usually pressure is not employed in reactions of this type because of the extra cost of capital equipment and processing. However, a reaction medium of higher volatility can render the use of pressures greater than atmospheric more practical. Typically, the pressure should not exceed about 20 psig and preferably from about 10 to 20 psig. In general, such pressures do not require expensive equipment. More preferably, the reaction is carried out at atmospheric pressure but as indicated pressures higher and lower than atmospheric can be used to conduct the reaction.

In general, the amount of reactants employed will be about the stoichiometric amounts. As indicated hereinabove, this means that for substantially complete substitution about two alkoxide, phenoxide or thiol derivative radicals are required for reaction with every phosphorus atom in the phosphorus-nitrogen structure. This, of course, does not preclude the use of a divalent alkoxy, phenoxy or thiol derivative radical in which full substantially complete substitution may be obtained with one radical for each phosphorus atom. In most instances, it is desirable to use a slight excess of the alkoxide, phenoxide or thiol derivative to insure substantially complete reaction with the phosphonitrilic halide. According to the invention, then about 0 to 15 mole equivalent excess of the alkali metal alkoxide, phenoxide or thiol derivative can be used per mole of phosphorus. When less than a stoichiometric amount of the alkoxide is to be used, an excess of the phosphonitrilic halide equivalent to the degree of substitution desired may be used. Thus, for about 50 percent substitution half the stoichiometric amount of the alkoxide, phenoxide or thiol derivative should be added.

In many instances the reactants are prepared in solvent which serves as a reaction medium. The reactants dissolved or dispersed in the reaction medium are then contacted under appropriate reaction conditions as described above and the reaction occurs. The amount of reaction medium in the dispersion or solution is not critical so long the dispersion or solution can be easily handled and the reactant maintained in the dispersion or solution. Generally, the concentration of reactants may range from about 10 to about 50 percent by weight in the reaction medium. Preferably, from about 22 to 35 percent by weight of the reactants may be dissolved or dispersed in the reaction medium.

As an illustration of the general reaction sequence the phosphazene compounds according to this invention can be prepared by adding the liquid aliphatic hydrocarbon reaction medium to a suitable reaction vessel equipped with heating means, stirring means, a reflux condenser and the necessary piping for addition of reactants. Then the alkali metal alkoxide, phenoxide or thiol derivative is added to the reaction vessel and the stirrer is activated to disperse the alkali metal alkoxide, phenoxide or thiol derivative into the reaction medium. Then the phosphonitrilic halide is added to the reaction vessel, while continuing the agitation. The heat of reaction brings the reaction mixture up to reaction temperature and cooling is applied while the remaining phosphonitrilic halide is added.

After completion of the phosphonitrilic halide addition, the temperature of the reaction mixture decreases. The heater is adjusted to maintain the desired temperature for a period of from one to five hours until the reaction is completed. The reaction mass is allowed to cool to ambient temperature. The reaction mass containing the substituted phosphazene is washed with water at least once and the aqueous layer separated. Then the reaction medium is distilled off leaving substantially pure substituted phosphazene product. The character of the product of course depends on the reactants and their concentration, the time and temperature of reaction. Other conditions as discussed hereinabove will also influence the type of product and degree of substitution.

In another preferred embodiment of the process of this invention, the alkali metal alkoxide, phenoxide or thiol derivative can be prepared in the liquid aliphatic hydrocarbon reaction medium and then the phosphonitrilic halide reacted with the alkali metal alkoxide, phenoxide or thiol derivative in the liquid aliphatic reaction medium. Therefore, in accord with this invention, a preferred process for the manufacture of phosphazene compounds comprises reacting an alkali metal and an alcohol or phenol reactant in a liquid saturated aliphatic hydrocarbon having from about 6 to about 12 carbon atoms in the molecule to produce a slurry of the alkali metal alkoxide or phenoxide in the hydrocarbon and then reacting a phosphonitrilic halide with the alkali metal alkoxide or phenoxide in a reaction medium comprising the liquid aliphatic hydrocarbon.

The alcohol or phenol reactant can be any of the alcohols or phenols described hereinabove. Preferably the reactant is a lower alkanol, which according to this invention can have from about one to about six carbon atoms. Preferably the alcohol or phenol reactant is propanol or phenol, and most preferably propanol. The saturated aliphatic hydrocarbon is preferably a paraffinic hydrocarbon which boils in the range of from about 90° to about 130°C and said reaction medium consists essentially of a mixture of said paraffinic hydrocarbon and an inert halohydrocarbon solvent. The paraffinic hydrocarbons and inert halohydrocarbons described hereinabove can be used in this particular embodiment. Also, the alkali metal can be any of those described above, with sodium being preferred. Therefore, a highly preferred embodiment of this process is one in which the alkali metal is sodium, the alcohol reactant is propanol and the saturated aliphatic hydrocarbon is a paraffinic hydrocarbon which boils in the range of from about 70° to about 150°C.

Illustrative non-limiting examples of this embodiment are the following.

EXAMPLE I

To a suitable reaction vessel containing a stirrer, heating means and reflux condenser was added heptane, 258.9 g, and metallic sodium, 39.1 g (1.7 moles). The mixture was heated to 116°C with 18 psig of pressure from the heptane. The stirrer was started when the sodium melted forming a dispersion of molten sodium in the heptane. To this mixture was added 112.4 g (1.87 moles) of n-propyl alcohol over a 20-minute period. The byproduct hydrogen was vented. After the propanol feed was discontinued, the heating with stirring was continued for approximately 30 minutes. To the resulting dispersion of sodium propoxide in heptane was added a solution of phosphonitrilic chloride in monochlorobenzene, about 350 g of 25.7 percent phosphonitrilic chloride (0.775 moles). The addition was completed over a 20-minute period. The pressure was reduced to atmospheric pressure and temperature controlled by external cooling of the reaction vessel to maintain a temperature of about 104°C during the addition. The mixture was refluxed at 104°C for about 3 hours, washed with water and evaporated to remove solvents. About 118.3 g (0.726 moles) of an oily liquid hexapropoxyphosphazene was obtained. This corresponds to a yield of about 93.7 percent based upon the phosphonitrilic chloride.

EXAMPLE II

To a reactor similar to that used in Example I was charged 50.6 g (22 moles) of metallic sodium and 335 g of n-octane. The reactor contents were heated to melt the sodium and the temperature was controlled at about 105°C under atmospheric pressure. The reactor contents were stirred to disperse the sodium in the n-octane. After dispersion, 145.4 g (2.42 moles) of n-propanol was added slowly over a period of 20 minutes. The unreacted propanol was condensed and returned to the reactor. Hydrogen evolved during the reaction and was vented. At the end of the propanol addition the slurry was slightly thick. Heating was continued for about 30 minutes at 105°C was continued stirring. The final slurry was fluid and creamy. The yield of sodium propoxide was about quantitative.

To the slurry of sodium propoxide in n-octane was added 116 g (1 mole) of phosphonitrilic chloride in 312.5 g of monochlorobenzene. The temperature was maintained at 105°C with outside cooling during the addition. After completion of the addition, heating of the mixture continued at 105°C for about 4 hours. It was then washed with water and the solvents stripped off. About 109 g (0.94 moles) of hexapropoxyphosphazene was obtained. This corresponds to a yield of about 94 percent based on the amount of phosphonitrilic chloride used.

EXAMPLE III

To a suitable reactor was added octane, 335 g, and metallic sodium, 50.6 g (2.2 moles). According to the procedure outlined in Example I, the mixture was heated to 87°C under atmospheric pressure. Methanol, 23.4 g (0.73 mole) was added over a 20-minute period. Temperature was allowed to rise from 87° to 105°C. Butanol, 108.8 g (1.47 moles) was added over a 12-minute period. Heating was continued for 30 minutes at 105°C. To the above slurry was added 116 g (1 mole) of mixed phosphonitrilic chloride in 259.7 g of monochlorobenzene as in Example I. The temperature was maintained at 105°C during the addition. After heating at 105°C for 4 hours, washing with water and stripping off the solvent, 112.8 g of mixed alkoxyphosphazene was obtained.

Similar results are obtained when the solvent used in the foregoing examples is replaced with hexane, cyclohexane, cycloheptane and like hydrocarbons having a boiling point within the range of about 70° to about 130°C. Also, the propanol can be replaced with methanol, ethanol, butanol, pentanol, hexanol, phenol, naphthol or their alkylated derivatives or mixtures of the foregoing alcohols and/or their alkylated derivatives with similar results. The sodium can be replaced with lithium or potassium with similar results. Also the monochlorobenzene can be replaced by sym-tetrachloroethane, dichlorobenzene and the like producing similar results.

Variations of the above process within the scope of this invention include
  preparation of an alkali metal alkoxide or phenoxide in a mixed solvent system, such as a 1:1 mixture of n-heptane and n-octane, and subsequent reaction with a phosphonitrilic halide;
  preparation of an alkali metal alkoxide or phenoxide suspended in a mixed solvent system and subsequent reaction of the suspension with a phosphonitrilic halide in a liquid halohydrocarbon; and
  preparation of an alkali metal alkoxide or phenoxide and a phosphonitrilic halide with reaction in a liquid aliphatic hydrocarbon reaction medium.

Of course, skilled practioners will recognize further variations in the process of this invention. The products of this invention can be used as fire retardants for cellulose materials, including fibers, filaments and fabrics. These materials may be applied to the cellulose by dipping, spraying, or other means utilized for treating the surface. Alternatively, for rayon and other regenerated cellulosics, one or more of the materials may be impregnated or added to the product by incorporation in the viscose prior to spinning. The amount of phosphonitrilic polymer flame retardant dispersed in the regenerated cellulose will vary from about 1 to about 30 weight percent and preferably from about 2 to about 20 weight percent based on the weight of the filament.

For impregnation prior to spinning and the finished materials, one may proceed according to the teachings of Godfrey U.S. Pat. No. 3,455,713. That patent is incorporated by reference herein as if fully set forth. Accordingly, one method of preparing cellulose filaments and filamentary articles according to this invention is to use the flame retardants provided herein according to the method set forth in Godfrey supra. Likewise, the instant invention provides regenerated cellulose filaments and filamentary articles prepared from the flame retardants, herein provided as incorporated utilizing the techniques set forth by Godfrey.

What is claimed is:

1. A process for the manufacture of phosphazene compounds consisting essentially of reacting alkali metal alkoxide having from 1 to about 6 carbon atoms or alkali metal phenoxide with a phosphonitrilic halide at from about 70° to about 150°C in a reaction medium consisting essentially of a liquid paraffinic hydrocarbon and an inert chloroaromatic hydrocarbon solvent.

2. The process of claim 1 wherein said paraffinic hydrocarbon is a paraffinic hydrocarbon having from about 6 to about 9 carbon atoms.

3. The process of claim 1 wherein said paraffinic hydrocarbon is a paraffinic hydrocarbon boiling within the range of from about 70° to about 150°C.

4. The process of claim 1 wherein said paraffinic hydrocarbon is a paraffinic hydrocarbon boiling within the range of from about 90° to about 130°C.

5. The process of claim 1 wherein said paraffinic hydrocarbon is heptane or octane or a mixture of heptane and octane.

6. The process of claim 1 wherein said chloroaromatic hydrocarbon solvent is chlorobenzene.

7. A process for the manufacture of phosphazene compounds consisting essentially of reacting an alkali metal alkoxide having from 1 to about 6 carbon atoms or alkali metal phenoxide with a phosphonitrilic halide at from about 70° to about 150°C, said process being further characterized by providing said alkali metal alkoxide or phenoxide in a liquid aliphatic hydrocarbon reaction medium and providing said phosphonitrilic halide in an aromatic halohydrocarbon reaction medium.

8. A process for the manufacture of phosphazene compounds which consists essentially of:
   a. forming a slurry of an alkali metal alkoxide or phenoxide by reacting an alkali metal with an alcohol having from 1 to about 6 carbon atoms or phenol in a liquid paraffinic hydrocarbon reaction medium;
   b. forming a solution of a phosphonitrilic halide in an inert liquid chloroaromatic hydrocarbon solvent;
   c. intermixing said slurry and said solution at from about 70° to about 150°C whereby a phosphazene product and alkali metal halide by-product are formed in the reaction mixture which comprises the liquid paraffinic hydrocarbon and the inert liquid chloroaromatic hydrocarbon solvent;
   d. separating the alkali metal halide by-product from the reaction mixture;
   e. separating the reaction mixture from the phosphazene; and
   f. separating the reaction mixture into liquid paraffinic hydrocarbon for recycle to (a) and inert liquid chloroaromatic solvent for recycle to (b).

* * * * *